US004001765B2

United States Statutory Invention Registration [19]

[11] Reg. Number: H1765

O'Phelan et al. [45] Published: Dec. 1, 1998

[54] IMPLANTABLE BATTERY AND DEVICE INCORPORATING AN INTERNAL FUSE

[76] Inventors: Michael J. O'Phelan, 6895 Upper 28th St. North, Oakdale, Minn. 55128; Nick A. Youker, 20840 Aztec St. NW., Oak Grove, Minn. 55303; John J. Hunt, 4895 Countryside Dr., Shoreview, Minn. 55126

[21] Appl. No.: 794,403

[22] Filed: Jan. 30, 1997

[51] Int. Cl.[6] ..... A61N 1/00

[52] U.S. Cl. ..... 607/1

[58] Field of Search ..... 607/2, 29, 34

*Primary Examiner*—Charles T. Jordan
*Assistant Examiner*—Meena Chelliah

[57] ABSTRACT

An implantable battery and device incorporating an internal fuse is disclosed. The internal fuse is incorporated into the implantable battery. Upon a malfunction within the device or the battery causing a greater than within specification current, the fuse blows. The blowing of the fuse effectively shuts off the battery, and protects it from overheating. In various embodiments, the fuse is a fusible link, or a thin metal or a material neck-down portion of the lithium or the silver vanadium oxide carrier which is unable to carry more than within specification current.

4 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

IMPLANTABLE BATTERY AND DEVICE INCORPORATING AN INTERNAL FUSE

FIELD OF THE INVENTION

The present invention relates in general to the field of implantable devices, and in particular to batteries for such devices having internal fuses.

BACKGROUND OF THE INVENTION

Devices implantable in the body for electrical cardioversion or pacing of the heart are well known. Specifically, devices implanted in or about the heart have been used to reverse (i.e., defibrillate or cardiovert) certain life-threatening arrhythmias, or to stimulate contraction (pacing) of the heart, where electrical energy is applied to the heart via electrodes to return the heart to its normal rhythm.

An implantable medical device usually includes an implantable battery in order to power the device. For example, a cardiac pacing unit typically includes pulse generating circuitry, electrodes to deliver signals to the heart and/or sense certain electrical signals made by the heart, and a battery. Because implantable device such as defibrillators are commonly expected to deliver a high jolt of energy to the heart when necessary, the battery in these instances is a high-energy power source.

Design engineers of such implantable medical devices are therefore concerned with the possibility of the battery rising in temperature, which at least causes discomfort to the host patient or tissue damage, and at worst can pose a potentially life-threatening situation. An electronic malfunction within an implantable device or in one of its components, for example, may cause the power source to rise in temperature. In rare cases, the battery itself may begin its own internal breakdown (i.e., chemical reaction), which can cause the battery to overheat.

To decrease the chance of the battery of an implantable medical device from rising in temperature, medical device design engineers commonly incorporate a fuse into the circuitry of the device. The fuse is designed such that should any of a predetermined certain number of components begin to malfunction, the fuse blows. This limits the current drawn from the battery, and prevents the battery from overheating.

However, there are several drawbacks to the inclusion of a fuse into the circuitry of an implantable device. first, the fuse is typically located in the portion of the charging circuit of the device that draws the most (i.e., the "high current" portion of the device). Such a fuse does not protect the battery against short circuits developing in other portions of the device that draw lower amount of current, which over time can still cause the battery to overheat.

Furthermore, typically the number of potential shorting points within a complex implantable medical device is great enough that it is very difficult to provide fuse protection for all such points. In these situations, the designer usually provides for fuse protection only in portions of the device that are more susceptive to shorting, and leaves unprotected those portions of the device that are less susceptible. The less susceptible portions may still, however, short and overheat the battery.

Because the fuse is included within a portion of the circuitry of the medical device, it also does not protect against the battery itself breaking down and overheating. Moreover, the inclusion of a fuse into the circuitry adds internal resistance, which causes resistance losses that are highly undesirable from a current drain standpoint. For example, a larger battery may be required to compensate for these losses. Finally, the inclusion of a fuse into the circuitry takes up valuable packaging real estate within the implantable device. This makes the device more unwieldy to use.

Therefore, there is a need for a fuse for an implantable device that overcomes these and other drawbacks.

SUMMARY OF THE INVENTION

The present invention describes an implantable battery and device that incorporates an internal fuse within the battery. The fuse is incorporated within the battery itself. Therefore, the invention protects against any short in the circuitry of the implantable device, and not only against shorts in a few selected portions of the circuitry. The invention also protects against breakdown within the battery from causing overheating. Because the fuse is internal to the battery, it does not take up circuitry real estate, and does not add to the internal resistance of the circuitry.

In various embodiments, the fuse is a fusible link, or a thin metal or a material neck-down portion of the lithium or the silver vanadium oxide carrier which is unable to carry more than within specification current.

DETAILED DESCRIPTION OF THE INVENTION

The present invention relates to an implantable battery and device having an internal fuse incorporated into the battery. In the following detailed description of the invention, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
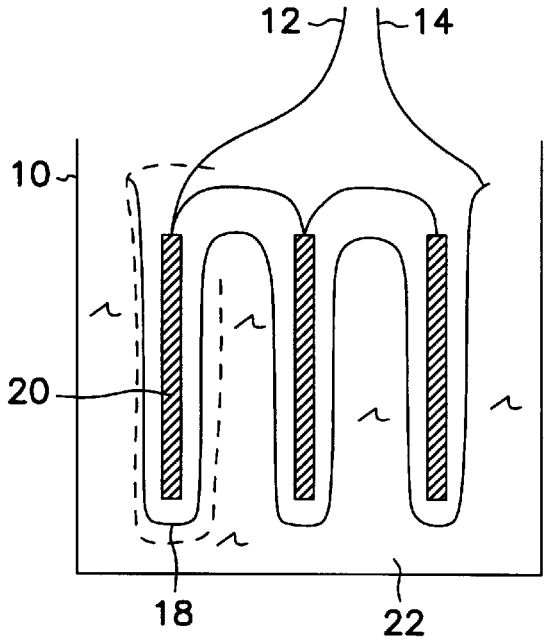
FIG. 1 is a diagram of a typical implantable battery in conjunction with which the present invention may be implemented.

Referring first to FIG. 1, a block diagram of a typical battery, in conjunction with which the present invention may be implemented, is shown. The battery of FIG. 1 has a housing 10, anode 12, and cathode 14. The battery is made up of at least one anode plate, such as anode plate 18, and at least one cathode plate, such as cathode plate 20. The plates are stacked into an accordion-type assembly with anode plates and cathode plates alternating from one side of the battery to the other. The cathode plates connect to one another as well as to cathode 12 in series. Likewise, the anode plates connect to one another as well as to anode 14 in series.

The anode and cathode plates are immersed in electrolytic solution 22. By immersion in electrolytic solution 22, a chemical reaction occurs and creates a voltage potential between anode 12 and cathode 14. Because the chemical reaction caused by the immersion of the anode and cathode plates in the electrolytic solution creates the voltage potential between anode 12 and cathode 14, the battery of FIG. 1 is known as a chemical reaction-based battery. Such a battery would be implanted into a host body along with an implantable medical device, such that anode 12 and cathode 14 are coupled to the medical device to provide it with a power source.

Figure 2:
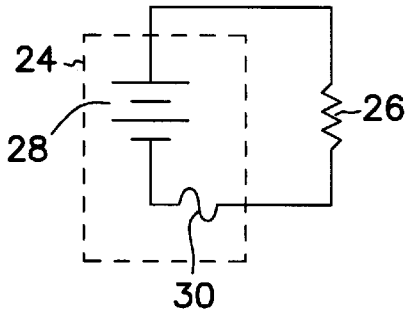
FIG. 2 is a schematic of an implantable battery and device according to the present invention.

Referring next to FIG. 2, a schematic of an implantable battery and device according to the present invention is shown. Battery 24 is coupled to load 26 such that battery 24 provides power to load 26. Battery 24 is an implantable battery, such as the battery shown in and described in conjunction with FIG. 1. Load 26 is an implantable device, such as a defibrillator. Battery 24 is specifically made up of a power generator 28 and internal fuse 30. One example of power generator 28 is the combination of anode plates, cathode plates, and electrolytic solution shown in and described in conjunction with FIG. 1.

Internal fuse 30 is internal to battery 24. When any portion of the circuitry of load 26 causes load 26 to draw greater than within specification amounts of current from battery 24, fuse 30 blows. That is, fuse 30 has a predetermined current rating, excess of which causes it to blow. This prevents power generator 28 of battery 24 from overheating, thereby protecting the host patient. Furthermore, internal fuse 30 blows when internal shorting within battery 24 (e.g., as a result of a chemical breakdown within generator 28) causes an out-of-specification current drain.

Incorporation of internal fuse 30 within battery 24, instead of within load 26, provides the present invention with a number of advantages. The design of power generator 28 takes into account the minute current drain that is inherently caused by fuse 30. Therefore, the design of load 26 does not have to take into account the internal resistance of fuse 30. Because it is internal to battery 24 and not load 26, fuse 30 also does not take up valuable packaging space within load 26.

Furthermore, fuse 30 provides complete protection in that it is blown when any part of load 26 malfunctions and causes a greater than within specification current drain. The design of load 26 does not have to include any fuse circuitry, which in any case would be disadvantageous in that protection for short circuits could be achieved in only certain parts of load 26, thereby not providing complete protection. Finally, fuse 30 provides complete protection in that it provides protection in the case where any part of battery 24 malfunctions as well.

Figure 3:
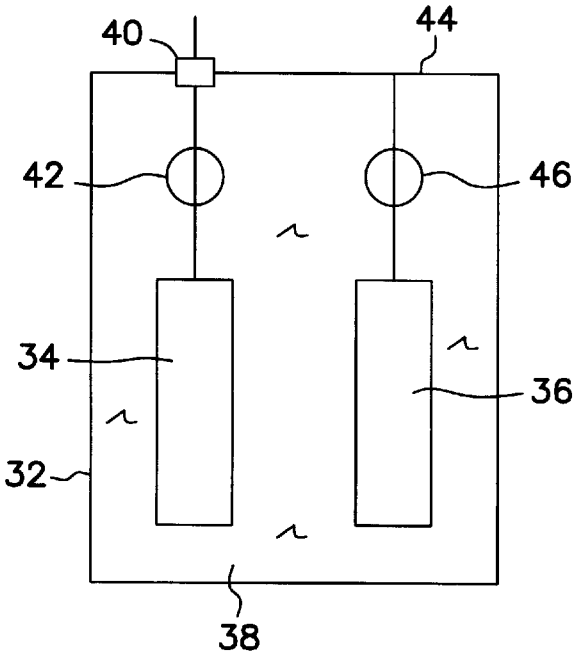
FIG. 3 is a diagram of an implantable battery illustrating one manner in which the invention can be implemented; and, FIG. 4 is a diagram showing one of the fuses of FIG. 3 in more detail.

Referring now to FIG. 3, a diagram of an implantable battery illustrating one manner in which the invention can be implemented is shown. The implantable battery of FIG.3 is one embodiment of, and thus corresponds to, battery 24 of FIG. 2. The implantable battery includes housing 32, within which one or more anode plates 34 and one or more cathode plates 36 are encased. For sake of clarity, only one anode plate 34 and one cathode plate 36 is shown in FIG. 3, however. Anode plate 34 and cathode plate 36 are immersed in electrolytic solution 38.

Anode plate 34 is connected to anode terminal 40 (i.e., an anode feed-through) through fuse 42, while cathode plate 36 is connected to cover 44 through fuse 46. Cover 44 is conductive, and directly attaches to housing 32, which is also conductive. Therefore, the entirety of housing 32 and cover 44 acts as a ground (i.e., a cathode) for the implantable battery of FIG. 3. Fuse 42 and fuse 46 together correspond to fuse 30 of battery 24 of FIG. 2. While as shown in FIG. 3 the invention includes both a fuse 42 and a fuse 46, in other embodiments of the invention only one of fuses 42 and 46 is present.

When the load to which the battery of FIG. 3 is coupled and to which it acts as a power supply malfunctions, causing a current drain greater than within specification, at least one of fuse 42 and fuse 46 blows. This creates a discontinuity in the circuit, effectively shutting off the battery, and preventing the battery from overheating. Likewise, in the case where the battery itself internally malfunctions (as a result, for example, of a chemical breakdown in its composition), at least one of fuse 42 and 46 blows, shutting off the battery and preventing it from overheating.

Figure 4:
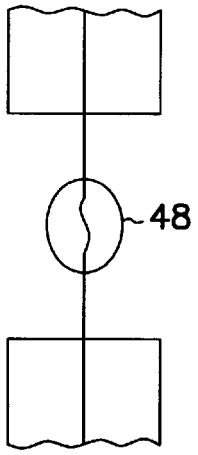

Referring now to FIG. 4, a diagram illustrating one of the fuses of FIG. 3 (i.e., fuse 42 and fuse 46) in more detail is shown. Fuse 48 is coupled to the anode plates and the anode terminal (in the case where fuse 48 corresponds to fuse 42 of FIG. 3), or to the cathode plates and the cover (in the case where fuse 48 corresponds to fuse 46 of FIG. 3), in series. Fuse 48 is designed so that it can withstand a current within specification. When a greater than specification current results from a battery or load malfunction, fuse 48 blows. Because it is connected in series, the resulting discontinuity effectively shuts off the battery.

The invention is not limited to any particular type of fuse 48. The fuse as shown in FIG. 4 is oriented vertically, but the invention is also not so limited. In other embodiments, the fuse is a fusible link, or a thin metal or a material neck-down portion of the lithium or the silver vanadium oxide carrier which is unable to carry more than within specification current.

It is to be understood that the above description is intended to be illustrative, and not restrictive. Many other embodiments will be apparent to those of ordinary skill within the art upon review of the above description.

What is claimed is:

1. An implantable system comprising:

an implantable device; and, an implantable battery providing power to the implantable device, wherein the implantable battery includes a fuse having a predetermined current rating.

2. The implantable system of claim 1, wherein the fuse protects the battery from overheating.

3. An implantable battery comprising:

a power generator; and, a fuse coupled to the power generator and having a predetermined current rating.

4. The implantable battery of claim 3, wherein the fuse protects the battery from overheating.

* * * * *